United States Patent [19]

Aoyama

[11] Patent Number: 5,516,951
[45] Date of Patent: May 14, 1996

[54] PROCESS FOR PREPARING 1,1,1,4,4,4-HEXAFLUORO-2-BUTENE AND 1,1,1,4,4,4-HEXAFLUOROBUTANE

[75] Inventor: Hirokazu Aoyama, Osaka, Japan

[73] Assignee: Daikin Industries Ltd., Osaka, Japan

[21] Appl. No.: 436,298

[22] PCT Filed: Nov. 18, 1993

[86] PCT No.: PCT/JP93/01690

§ 371 Date: May 19, 1995

§ 102(e) Date: May 19, 1995

[87] PCT Pub. No.: WO94/12454

PCT Pub. Date: Jun. 9, 1994

[30] Foreign Application Priority Data

Nov. 20, 1992 [JP] Japan .................................. 4-335315

[51] Int. Cl.$^6$ .................. C07C 17/263; C07C 17/354; C07C 19/08; C07C 21/18
[52] U.S. Cl. .................................. 570/175; 570/153
[58] Field of Search .................................. 570/153, 175

[56] References Cited

U.S. PATENT DOCUMENTS

| | | | |
|---|---|---|---|
| 2,550,953 | 5/1951 | Barrick | 570/175 |
| 4,739,123 | 4/1988 | Furutaka et al. | 570/153 |
| 4,760,208 | 7/1988 | Saran | 570/153 |
| 5,382,720 | 1/1995 | Ikawa et al. | 570/153 |

*Primary Examiner*—Joseph E. Evans
*Attorney, Agent, or Firm*—Birch, Stewart, Kolasch & Birch

[57] ABSTRACT

1,1,1,4,4,4-Hexafluoro-2-butene is prepared by reacting 1,1,1-trifluoro-2,2-dichloroethane with copper and an amine, and then 1,1,1,4,4,4-hexafluorobutane is prepared by reacting 1,1,1,4,4,4-hexafluoro-2-butene with hydrogen.

1,1,1,4,4,4-Hexafluorobutane, which is used as a coolant, a blowing agent or a cleaner and can reserves the environment, is easily obtained, and 1,1,1,4,4,4-hexafluoro-2-butene, which is useful as an intermediate for the 1,1,1,4,4,4-hexafluorobutane, or as a monomer of fluorine-containing polymers is easily prepared in a good yield.

5 Claims, No Drawings

PROCESS FOR PREPARING 1,1,1,4,4,4-HEXAFLUORO-2-BUTENE AND 1,1,1,4,4,4-HEXAFLUOROBUTANE

FIELD OF THE INVENTION

The present invention relates to a process for preparing 1,1,1,4,4,4-hexafluoro-2-butene and 1,1,1,4,4,4-hexafluorobutane.

1,1,1,4,4,4-Hexafluorobutane (hereinafter referred to as "HFC-356mff") is one of compounds which can substitute for chlorofluorocarbons or hydrochlorofluorocarbons used as coolants, blowing agents, cleaners, etc.

1,1,1,4,4,4-Hexafluoro-2-butene (hereinafter referred to as "HFC-1336") is useful as an intermediate for the production of compounds which can substitute for chlorofluorocarbons or hydrochlorofluorocarbons used as coolants, blowing agents, cleaners, etc., or as a monomer of fluorine-containing polymers.

PRIOR ART

In these years, serious attentions have been paid on preservation of environment, and hydrofluorocarbons, which can substitute for chlorofluorocarbons or hydrochlorofluorocarbons used as coolants, blowing agents, cleaners, etc., have been studied and selected. In connection therewith, a process for easy preparation of such hydrofluorocarbon or an intermediate for its production has been sought.

In general, HFC-356mff is easily prepared by adding hydrogen to HFC-1336. Then, a process for easy and effective preparation of HFC-1336 is required. However, any process for the effective preparation of HFC-1336 has not been proposed.

1,1,1-Trifluoro-2,2-dichloroethane (hereinafter referred to as "HCFC-123") is an easily available cheap raw material. But, no process for preparing HFC-1336 from HCFC-123 has been known.

SUMMARY OF THE INVENTION

An object of the present invention is to provide a process for preparing HFC-1336 from HCFC-123 in a high yield.

Another object of the present invention is to provide a process for preparing HFC-356mff by further reacting HFC-1336 which is obtained by the above process with hydrogen.

According to the present invention, there is provided a process for preparing HFC-1336 comprising reacting HCFC-123 with copper, in particular, metal copper and an amine.

Further, according to the present invention, there is provided a process for preparing HFC-356mff comprising reacting HFC-1336 which is prepared by the above process with hydrogen.

The processes of the present invention are based on the finding that, when HCFC-123 is reacted with metal copper and an amine, unexpectedly, a reductive coupling reaction takes place, and HFC-1336 is readily formed in a good yield.

DETAILED DESCRIPTION OF THE INVENTION

In the process of the present invention, HCFC-123 as the starting material is known to be easily prepared at a low cost.

As the copper to be used in the present invention, metal copper, that is, copper having the valency of 0 (zero) is preferably used. In view of a speed of the reaction, a preferred shape of copper is a flake-shape, a granule, or a powder.

An amount of copper is not critical. Preferably, copper is used in a molar amount equal to, or one to 5 times larger than the amount of HCFC-123.

A kind of the amine to be used in the present invention is not limited and can be selected from a wide variety of amines. Preferred examples of the amine are aliphatic primary amines such as methylamine, ethylamine, n-propylamine, isopropylamine, n-butylamine, sec.-butylamine, octylamine, etc.; aliphatic secondary amines such as dimethylamine, diethylamine, di-n-propylamine, diisopropylamine, di-n-butylamine, dioctylamine, etc.; aliphatic tertiary amines such as trimethylamine, triethylamine, tri-n-propylamine, triisopropylamine, tri-n-butylamine, trioctylamine, etc.; cyclic amines such as morpholine, piperazine, piperidine, pyrrolidine, etc.; alkanolamines such as mono-, di- and triethanolamines; and ammonia.

Among them, the aliphatic primary amines such as methylamine, ethylamine, propylamine, butylamine, sec.-butylamine, etc., and the aliphatic secondary amines such as dimethylamine, diethylamine, di-n-propylamine, diisopropylamine, di-n-butylamine, etc. are preferred.

An amount of the amine used in the present invention is not limited. Preferably, the amine is used in a molar amount equal to, or one to 5 times larger than the amount of HCFC-123.

In the process of the present invention, the reaction can be carried out in a batch manner or a continuous manner. In general, the reaction is carried out as follows:

In a pressure vessel equipped with a stirrer such as an autoclave, determined amounts of HCFC-123, metal copper and the amine are charged and reacted, or the determined amounts of HCFC-123 and metal copper are charged in a glass reactor equipped with a reflux condenser, and then the amine is dropwise added.

In the process of the present invention, a solvent may be used as a reaction medium. Preferred examples of the solvent are aprotic solvents, for example, ethers such as ethyleneglycol dimethyl ether, diethyleneglycol dimethyl ether, dioxane, etc.; ketones such as acetone, methyl ethyl ketone, etc.; amides such as dimethylformamide, dimethylacetamide, N-methylpyrrolidone, etc.; halogenated hydrocarbons such as methylene chloride, etc.; and so on.

A reaction temperature in the reaction of HCFC-123, metal copper and the amine is not critical, and usually from 10° to 120° C.

HFC-356mff is easily obtained by the addition of hydrogen to HFC-1336 which is prepared by the process of the present invention. HFC-356mff is useful as a blowing agent, a coolant or a cleaner which does not destroy the ozone layer.

The addition of hydrogen to HFC-1336 may be carried out by any of known methods. Production conditions will be explained briefly. When the reaction is carried out in a gas phase, a molar ratio of HFC-1336 to hydrogen is from 1:1 to 1:5, preferably from 1:1.5 to 1:3.

A reaction temperature is from 0° to 300° C., preferably from 20° to 200° C.

As a catalyst, noble metals such as platinum, palladium, ruthenium, etc. may be used. The catalyst may be carried on a carrier such as activated carbon, alumina, titania, zirconia, and so on, in a concentration of 0.01 to 10 wt. %, preferably 0.3 to 5 wt. %.

To the catalyst, a metal or metals such as silver, copper, zinc, etc. may be added.

In the hydrogen addition reaction in a liquid phase, HFC-1336 and a catalyst in an amount of 1 to 30 wt. %, preferably 3 to 20 wt. % based on the weight of HFC-1336 are charged in a pressure reactor, and an interior atmosphere is evacuated. Then, hydrogen is supplied. A pressure of hydrogen is not limited. In view of the economy of the reactor, a pressure of 5 to 30 kg/cm$^2$G is preferred. Hydrogen may be supplemented with the progress of the reaction. An amount of hydrogen is form 1 to 1.5 moles per one mole of HFC-1336. A reaction temperature is preferably from 0° to 200° C., in particular, from 0° to 100° C.

A solvent may be used. As the solvent, those exemplified above and alcohols such as methanol, ethanol, isopropanol and so on may be used.

EXAMPLES

The present invention will be illustrated by the concrete examples, which do not limit the scope of the present invention.

EXAMPLE 1

In a 200 ml stainless steel autoclave equipped with a stirrer, copper powder (31.8 g), diethylamine (36.5 g) and HCFC-123 (76.5 g) were charged. After cooling the content to −60° C., the autoclave was evacuated, and then nitrogen was introduced. These procedures were repeated three times. After replacing the interior atmosphere by nitrogen, the temperature was raised to room temperature and thereafter to 60° C. while stirring.

After 10 hours of the reaction, the autoclave was cooled to room temperature. The content was collected in a trap cooled at −70° C. under reduced pressure. The recovered liquid weight was 59 g.

The recovered liquid was analyzed by gas chromatography. The results are shown in Table 1.

TABLE 1

|  | GC %[2)] |
|---|---|
| $CF_3CH=CHCF_3$[1)] | 43 |
| $CF_3CH_2Cl$ | 0.5 |
| $CF_3CHCl_2$ | 54.5 |
| Others | 2 |

Notes:
[1)]In this case, $CF_3CH=CHCF_3$ (HFC-1336) is a mixture of cis and trans isomers.
[2)]Selectivities in the gas chromatography analysis.

EXAMPLE 2

In the same manner as in Example 1 except that the charged amounts were changed as follows, the reaction was carried out. The recovered amount in the trap was 13.2 g.

| Copper powder | 25.4 g |
|---|---|
| Diethylamine | 29.2 g |
| HCFC-123 | 30.6 g |

The analysis was carried out in the same manner as in Example 1. The results are shown in Table 2.

TABLE 2

|  | GC %[2)] |
|---|---|
| $CF_3CH=CHCF_3$[1)] | 92 |
| $CF_3CH_2Cl$ | 2.5 |
| $CF_3CHCl_2$ | 0.5 |
| Others | 5 |

Notes:
1) and 2) See the Notes to Table 1.

EXAMPLE 3

In a 200 ml glass reactor equipped with a condenser which was kept at 5° C. and connected to a trap cooled at −70° C., a thermometer and a dropping funnel, copper powder (25.4 g) and HCFC-123 (30.6 g) were charged. While stirring the mixture with a magnetic stirrer, diethylamine (29.2 g) was dropped from the dropping funnel over about 3 hours. During this period, the reactor was heated or optionally cooled to maintain the interior temperature at 25° to 30° C.

After the addition of diethylamine, the stirring was continued for 2 hours at 25° to 30° C. Then, the reaction mixture was collected by the cold trap. An amount of the recovered liquid was 58 g. The recovered liquid was analyzed by gas chromatography. The results are shown in Table 3.

TABLE 3

|  | GC %[2)] |
|---|---|
| $CF_3CH=CHCF_3$[1] | 41 |
| $CF_3CH_2Cl$ | 0.8 |
| $CF_3CHCl_2$ | 55.7 |
| Others | 2.5 |

Notes:
1) and 2) See the Notes to Table 1.

EXAMPLE 4

In the same manner as in Example 1 except that n-butylamine was used in place of diethylamine and the charged amounts were changed as follows, the reaction was carried out. The recovered amount in the trap was 60 g.

| Copper powder | 31.8 g |
|---|---|
| n-Butylamine | 36.5 g |
| HCFC-123 | 76.5 g |

The analysis was carried out in the same manner as in Example 1. The results are shown in Table 4.

TABLE 4

|  | GC %[2)] |
|---|---|
| $CF_3CH=CHCF_3$[1)] | 44 |
| $CF_3CH_2Cl$ | 0.6 |
| $CF_3CHCl_2$ | 54.0 |
| Others | 1.4 |

Notes:
1) and 2) See the Notes to Table 1.

From the above results, it is understood that HFC-1336 can be obtained in a good yield when HCFC-123 is reacted with copper and an amine.

EXAMPLE 5

In a SUS-316 made reactor tube (a diameter of 20 mm), 0.5% palladium/activated carbon (10 cc) was filled. The interior of the tube was purged with nitrogen, and hydrogen was flowed at a flow rate 40 cc/min. Then, HFC-1336 was started to flow at a flow rate of 20 cc/min. Because of the exothermic reaction, the reaction tube was cooled from outside to keep the interior temperature of the tube at 50° C. An exit gas from the reactor tube was washed with water and analyzed by gas chromatography to find that a conversion of raw material HFC-1336 was 100%, and a selectivity of HFC-356mff was 99.7%.

EXAMPLE 6

In a 200 ml SUS-316 made autoclave, 3% palladium/carbon powder (5 g) was charged. After evacuating the interior of the autoclave, the autoclave was cooled to −40° C., and HFC-1336 (100 g) was charged. After rasing the autoclave temperature to room temperature, hydrogen was supplied up to 15 kg/cm$^2$G while stirring. Because of the exothermic reaction, the autoclave was cooled from outside to keep the interior temperature at 30° C. Since the pressure dropped with the progress of the reaction, the pressure was increased up to 15 kg/cm$^2$G by hydrogen. These procedures were repeated, and the reaction was continued till the hydrogen pressure did not drop. The autoclave was cooled to −20° C., and hydrogen was purged. Thereafter, the content in the autoclave was collected in a cold trap cooled at −70° C. under reduced pressure. An amount of the collected organic material was 98 g. According to the gas chromatography analysis, the conversion of HFC-1336 was 100%, and the selectivity of HFC-356mff was 98%.

EFFECTS OF THE INVENTION

According to the present invention, HFC-1336 which is one of industrially important compounds is easily prepared in a good yield by a novel process. Further, from HFC-1336, HFC-356mff is prepared in an economical way.

What is claimed is:

1. A process for preparing 1,1,1,4,4,4-hexafluoro-2-butene comprising reacting 1,1,1-trifluoro-2,2-dichloroethane with copper and an amine.

2. The process according to claim 1, wherein said copper is metal copper having the valency of 0 (zero), and said amine is an aliphatic amine.

3. The process according to claim 1, wherein an amount of each of metal copper and said amine is at least an equimolar to 1,1,1-trifluoro-2,2-dichloroethane.

4. The process according to claim 1, wherein a reaction temperature in reacting 1,1,1-trifluoro-2,2-dichloroethane with metal copper and said amine is from 10° to 120° C.

5. A process for preparing 1,1,1,4,4,4-hexafluorobutane comprising reacting 1,1,1,4,4,4-hexafluoro-2-butene, which is prepared by a process of any one of claims 1 to 4, with hydrogen.

* * * * *